(12) United States Patent
Miki et al.

(10) Patent No.: US 7,977,671 B2
(45) Date of Patent: Jul. 12, 2011

(54) COMPOUND HAVING OXADIAZOLE RING STRUCTURE SUBSTITUTED WITH PYRIDYL GROUP AND ORGANIC ELECTROLUMINESCENCE DEVICE

(75) Inventors: Tetsuzo Miki, Tsukuba (JP); Makoto Nagaoka, Tsukuba (JP); Shuichi Hayashi, Tsukuba (JP); Yoshio Taniguchi, Ueda (JP); Musubu Ichikawa, Ueda (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 0 days.

(21) Appl. No.: 12/622,125

(22) Filed: Nov. 19, 2009

(65) Prior Publication Data
US 2010/0066244 A1 Mar. 18, 2010

Related U.S. Application Data

(62) Division of application No. 10/594,241, filed as application No. PCT/JP2005/006420 on Mar. 25, 2005, now Pat. No. 7,812,341.

(30) Foreign Application Priority Data

Mar. 25, 2004 (JP) ................................ 2004-088909
Mar. 25, 2004 (JP) ................................ 2004-089277

(51) Int. Cl.
*H01L 35/24* (2006.01)
*H01L 51/00* (2006.01)
(52) U.S. Cl. .............. 257/40; 257/E51.001; 548/131; 548/132; 548/143; 548/144; 548/145
(58) Field of Classification Search .............. 257/40, 257/E51.001; 548/131, 132, 143, 144, 145
See application file for complete search history.

(56) References Cited

U.S. PATENT DOCUMENTS
2004/0155238 A1* 8/2004 Thompson et al. ............. 257/40
2009/0102361 A1 4/2009 Miki et al.

FOREIGN PATENT DOCUMENTS
JP 54-2739 1/1979
(Continued)

OTHER PUBLICATIONS
Cea et al, "A blended layer MEH-PPV electroluminescent device incorporating a new electron transport material," Materials Science and Engineering, C, 22, (2002), pp. 87-89.*

(Continued)

*Primary Examiner* — Kenneth A Parker
*Assistant Examiner* — Anthony Ho
(74) *Attorney, Agent, or Firm* — Oblon, Spivak, McClelland, Maier & Neustadt, L.L.P.

(57) ABSTRACT

The present invention relates to a compound having an oxadiazole ring structure having a substituted pyridyl group connected thereto, represented by the following general formula (1).

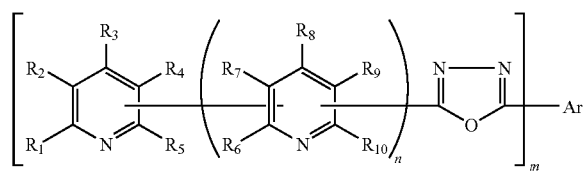

According to the present invention, it becomes possible to provide an organic compound having excellent characteristic of high stability in a thin film state, and the emission efficiency and durability of conventional organic EL devices can be remarkably improved.

25 Claims, 12 Drawing Sheets

FOREIGN PATENT DOCUMENTS

| | | |
|---|---|---|
| JP | 8-3147 | 1/1996 |
| JP | 8-3148 | 1/1996 |
| JP | 8-3150 | 1/1996 |
| JP | 8-48656 | 2/1996 |
| JP | 8-176148 | 7/1996 |
| JP | 2721442 | 11/1997 |
| JP | 2734341 | 1/1998 |
| JP | 3194657 | 6/2001 |
| JP | 3316236 | 6/2002 |
| JP | 3486994 | 10/2003 |

OTHER PUBLICATIONS

Po King Ng, et al., "The Role of Ruthenium and Rhenium Diimine Complexes in Conjugated Polymers That Exhibit Interesting Opto-Electronic Properties", Chemistry –A European Journal, vol. 7, No. 20, 2001,pp. 4358-4367.

Chemical Abstracts, AN 2001:389558, vol. 135, Abs. No. 204364, May 30, 2001, 3 pages.

Changsheng Wang, et al., "Polymeric Alkoxy PBD [2-(4-Biphenylyl)-5-Phenyl-1,3,4-OXADIAZOLE] for Light-Emitting Diodes", Advanced Functional Materials, vol. 11, No. 1, Feb. 2001, pp. 47-50.

Vincent J. Catalano, et al., "Monometallic and Dimetallic Ruthenium(II)-Terpyridine Complexes Employing the Tetradentate Ligands Dipyridylpyrazolyl, Dipyridyloxadlazole, and Their Dimethyl Derivatives", Inorganic Chemistry, vol. 42, No. 2, 2003, pp. 321-324.

Chishio Hosokawa, et al., Applied Physics, $9^{th}$ Lecture, Extended Abstract, 2001, pp. 55-61.

Takeo Wakimoto, "Optimization of Driving Lifetime Durability in Organic LED Devices Using Phosphorescent Guest Emitter", Applied Physics, $9^{th}$ Lecture, 2001, pp. 23-31.

Chihaya Adachi, et al., "Electroluminescence in Organic Films With Three-Layer Structure", Japanese Journal of Applied Physics, vol. 27, No. 2, Feb. 1988, pp. 269-271.

R. D. Chambers, et al., "Polyfluoroheterocyclic Compounds. Part XIV1 Some Reactions of Tetrafluoroisonicotinic Acid and Pentafluorobenzoic Acid", Journal of the Chemical Society, No. 15, XP003018577, Jan. 1, 1968, pp. 1933-1937.

U.S. Appl. No. 12/966,181, filed Dec. 13, 2010, Miki, et al.

* cited by examiner

COMPOUND HAVING OXADIAZOLE RING STRUCTURE SUBSTITUTED WITH PYRIDYL GROUP AND ORGANIC ELECTROLUMINESCENCE DEVICE

TECHNICAL FIELD

The present invention relates to a compound and a device, suitable to an organic electroluminescence (EL) device which is a self-luminescent device suitable to various display devices, and particularly the invention relates to a compound having an oxadiazole ring structure having a substituted pyridyl group connected thereto, and an organic EL device using the compound.

BACKGROUND ART

Because an organic EL device is a self-luminescent device, it is luminous, excellent in visibility, and capable of giving clear display, as compared with a liquid crystal device. Therefore, active investigations have been made.

C. W. Tang et al. of Eastman Kodak Company developed a two-layer type laminated structure element in 1987, and this enabled an organic EL device using an organic substance to be put into practical use. They laminated an electron transporting fluorescent substance and a hole transporting organic substance, and injected both charges in a layer of the fluorescent substance to make the layer emit, thereby making it possible to attain high luminance of 1,000 cd/m$^2$ or more at a voltage of 10V or lower (for example, see Patent Document 1 and Patent Document 2).
Patent Document 1: JP-A-8-48656
Patent Document 2: Japanese Patent No. 3194657

Up to the present, many improvements have been made to put an organic EL device into practical use. High efficiency and durability are achieved by an electroluminescence device in which the role of two layers is further finely divided, and an anode, a hole injecting layer, hole transporting layer, an emission layer, an electron transporting layer, an electron injecting layer and a cathode are provided successively on a substrate (for example, see Non-Patent Document 1).
Non-Patent Document 1: The Japan Society of Applied Physics, 9$^{th}$ Lecture, Extended Abstract, pages 55-61 (2001)

Further, for the purpose of further improvement of emission efficiency, utilization of a triplet excitation is attempted, and utilization of a phosphorescent substance is investigated (for example, see Non-Patent Document 2).
Non-Patent Document 2: The Japan Society of Applied Physics, 9$^{th}$ Lecture, Extended Abstract, pages 23-31 (2001)

The emission layer may be prepared by doping an electron transporting compound generally called a host material with a fluorescent substance or a phosphorescent substance. As described in the above extended abstracts, selection of an organic material in an organic EL device greatly affects various characteristics such as efficiency and durability of the device, etc.

In an organic EL device, emission is obtained by recombination of electric charges injected from both electrodes in an emission layer. However, because hole mobility is higher than electron mobility, efficiency reduction due to that part of holes passes through the emission layer becomes problematic. For this reason, an electron transporting material having high electron mobility is demanded.

Tris(8-hydroxyquinoline)aluminum (hereinafter referred to as Alq) that is a representative emission material is generally used as an electron transporting material, but it is said that the electron mobility therewith is slow. For this reason, as a material having high mobility, for example, 2-(4-biphenylyl)-5-(4-t-butylphenyl)-1,3,4-oxadiazole (hereinafter referred to as PBD) was proposed (for example, see Non-Patent Document 3).
Non-Patent Document 3: Jpn. J. Appl. Phys., 27, L269 (1988)

However, it is pointed out that PBD is poor in stability in a thin film state such that it is liable to cause crystallization, and various oxadiazole derivatives have been proposed (for example, see Patent Documents 3 to 5).
Patent Document 3: Japanese Patent No. 2721442
Patent Document 4: Japanese Patent No. 3316236
Patent Document 5: Japanese Patent No. 3486994

In those electron transporting materials, although stability was improved as compared with PBD, it cannot be considered as sufficient, and from the standpoint of balance with a hole mobility, the electron mobility was still insufficient. For this reason, there were many cases that Alq having good stability is used as the electron transporting material, but satisfactory device characteristics were not obtained.

Further, as measures of preventing part of holes from passing through an emission layer and improving probability of recombination of electric charges in the emission layer, there is a method of inserting a hole blocking layer. As a hole blocking material, triazole derivatives (for example, see Patent Document 6), bathocuproine (hereinafter referred to as BCP), a mixed rigand complex of aluminum (BAlq) (for example, see Non-Patent Document 2) and the like are hitherto proposed.
Patent Document 6: Japanese Patent No. 2734341

However, in either material, film stability is insufficient, or function to block holes is insufficient. A hole blocking material generally used at present is BCP. However, BCP is not considered as a sufficiently stable material, so that it is not considered as sufficiently functioning as a hole blocking layer. Thus, satisfactory device characteristics were not obtained.

To improve device characteristics of an organic EL device, an organic compound having excellent electron injecting and transporting performances and hole blocking ability, and high stability in a thin film state is demanded.

DISCLOSURE OF THE INVENTION

Problems that the Invention is to Solve

One object of the present invention is to provide an organic compound having such excellent characteristics as having excellent electron injecting and transporting performances, having a hole blocking ability and having high stability in a thin film state, as a material for an organic EL device of high efficiency and high durability.

Another object of the present invention is to provide an organic EL device of high efficiency and high durability using the compound.

As physical characteristics of an organic compound suitable for the present invention, there can be exemplified that (1) electron injection property is good, (2) electron mobility is high, (3) hole blocking ability is excellent, and (4) thin film state is stable. Further, as physical characteristics of a device suitable for the present invention, there can be exemplified that (1) emission efficiency is high, (2) emission initiation voltage is low, (3) practical driving voltage is low, and (4) the maximum emission luminance is high.

Means for Solving the Problems

To achieve the above objects, the present inventors paid attention to the fact that the nitrogen atom of a pyridine ring which is electron-affinic has an ability to coordinate with a metal. They have designed and chemically synthesized a novel compound in which a substituted pyridine ring is connected to an oxadiazole ring, experimentally prepared various organic EL devices using the compound, and closely investigated characteristic evaluation of the devices, as a result, leading to the completion of the present invention.

That is, the above objects have been achieved by providing the following compounds.

(1) A compound having an oxadiazole ring structure having a substituted pyridyl group connected thereto, represented by the following general formula (1):

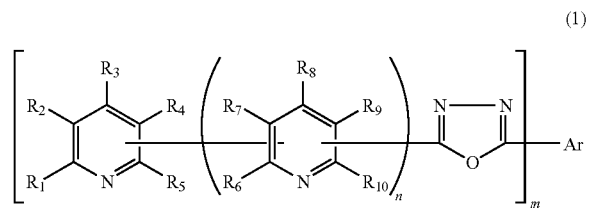

wherein Ar represents a substituted or unsubstituted aromatic hydrocarbon group, a substituted or unsubstituted aromatic heterocyclic group or a substituted or unsubstituted condensation polycyclic aromatic group; one of $R_1$, $R_2$, $R_3$, $R_4$ and $R_5$ is a linking group, and the others may be the same or different and represent a hydrogen atom, a fluorine atom, a cyano group, an alkyl group, a substituted or unsubstituted phenyl group or a substituted or unsubstituted naphthyl group; two of $R_6$, $R_7$, $R_8$, $R_9$ and $R_{10}$ are linking groups, and the others may be the same or different and represent a hydrogen atom, a fluorine atom, a cyano group, an alkyl group, a substituted or unsubstituted phenyl group or a substituted or unsubstituted naphthyl group; m is an integer of from 1 to 3; and n is an integer of from 0 to 4, provided that when n=0, four groups of $R_1$, $R_2$, $R_3$, $R_4$ and $R_5$ excluding the linking group are not simultaneously a hydrogen atom.)

(2) The compound having an oxadiazole ring structure as described in (1) above, wherein n in the general formula (1) is 1.

(3) The compound having an oxadiazole ring structure as described in (1) above, wherein n in the general formula (1) is 2.

(4) The compound having an oxadiazole ring structure as described in (1) above, wherein n in the general formula (1) is 0, and one of four groups of $R_1$, $R_2$, $R_3$, $R_4$ and $R_5$ excluding the linking group is a phenyl group.

Further, the present invention provides an organic electroluminescence device comprising a pair of electrodes, and at least one organic layer interposed therebetween, wherein the compound is contained as a structural material of the at least one organic layer.

As the aromatic hydrocarbon group, aromatic heterocyclic group or condensation polycyclic group in the substituted or unsubstituted aromatic hydrocarbon group, substituted or unsubstituted aromatic heterocyclic group, and substituted or unsubstituted condensation polycyclic aromatic group, represented by Ar in the general formula (1), specifically there are exemplified a phenyl group, a biphenyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a furanyl group, a pyronyl group, a thiophenyl group, a quinolyl group, a benzofuranyl group, a benzothiophenyl group, indolyl group, a carbazolyl group, a benzoxazolyl group, quinoxalyl group, a benzimidazolyl group, a pyrazolyl group, a dibenzofuranyl group, a dibenzothiophenyl group, and the like.

As substituents in the substituted or unsubstituted aromatic hydrocarbon group, substituted or unsubstituted aromatic heterocyclic group, and substituted or unsubstituted condensation polycyclic aromatic group, represented by Ar in the general formula (1), specifically there are exemplified a fluorine atom, a chlorine atom, a cyano group, a hydroxyl group, a nitro group, an alkyl group, an alkoxy group, an amino group, a substituted amino group, a trifluoromethyl group, a phenyl group, a tolyl group, a naphthyl group, an aralkyl group and the like.

As the substituted pyridyl group in the general formula (1), specifically a dipyridyl group, a terpyridyl group and a phenylpyridyl group can be exemplified.

The compound having an oxadiazole ring structure having a substituted pyridyl group connected thereto, represented by the general formula (1) of the present invention has electron mobility higher than the conventional electron transporting material, and excellent hole blocking ability, and is stable in a thin film state.

The compound having an oxadiazole ring structure having a substituted pyridyl group connected thereto, represented by the general formula (1) of the present invention can be used as a structural material for an electron transporting layer of an organic EL device. By using a material having electron injecting and transferring rates higher than the conventional materials, there can be given the effects that electron transporting efficiency of from an electron transporting layer to an emission layer improves, thereby improving emission efficiency, and additionally, driving voltage is decreased, thereby improving durability of an organic EL device.

The compound having an oxadiazole ring structure having a substituted pyridyl group connected thereto, represented by the general formula (1) of the present invention can also be used as a structural material for a hole blocking layer of an organic EL device. By using a material having excellent electron transporting property, as compared with the conventional material, as well as excellent hole blocking ability, and having high stability in a thin film state, there can be given the effects that driving voltage is decreased, current resistance is improved, and the maximum emission luminance of an organic EL device is improved, while having high emission efficiency.

The compound having an oxadiazole ring structure having a substituted pyridyl group connected thereto, represented by the general formula (1) of the present invention can also be used as a structural material for an emission layer of an organic EL device. By using a material of the present invention having excellent electron transporting property and broad band gap, as compared with the conventional material, as a host material of an emission layer and using as an emission layer by supporting a fluorescent substance or a phosphorescent substance, called a dopant, there can be give the effects that driving voltage is decreased, and an organic EL device having improved emission efficiency can be realized.

The organic EL device of the present invention uses the compound having an oxadiazole ring structure having a substituted pyridyl group connected thereto, which has electron transfer higher than the conventional electron transporting material, and excellent hole blocking ability, and is stable in a thin film state. Therefore, it becomes possible to realize high efficiency and high durability.

Advantage of the Invention

The present invention relates to the compound having an oxadiazole ring structure having a substituted pyridyl group connected thereto, useful as a structural material for an electron transporting layer, a hole blocking layer or an emission layer of an organic EL device, and also relates to the organic EL device prepared using the compound. Emission efficiency and durability of the conventional organic EL device could remarkably be improved by the present invention.

Figure 1:
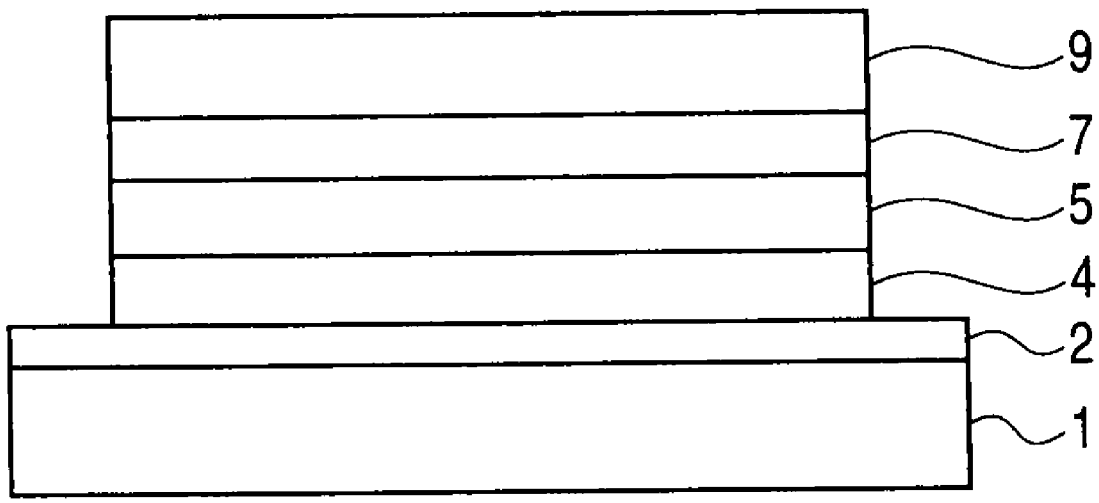
FIG. 1 is a view showing an EL device structure of Example 19.

Reference numerals and symbols in the drawings are as follows.

1: Glass substrate
2: Transparent anode
3: Hole injecting layer
4: Hole transporting layer
5: Emission layer
6: Hole blocking layer
7: Electron transporting layer
8: Electron injecting layer
9: Cathode

BEST MODE FOR CARRYING OUT THE INVENTION

The compound having an oxadiazole ring structure having a substituted pyridyl group connected thereto of the present invention is a novel compound, and those compounds can be synthesized by, for example, condensing 6-(2H-tetrazol-5-yl)-2,2'-bipyridine or the corresponding terpyridine or phenylpyridine with various aromatic acid chlorides.

Of the compounds having an oxadiazole ring structure having a substituted pyridyl group connected thereto, represented by the general formula (1), specific examples of the preferable compound are shown below, but the invention is not limited to those compounds.

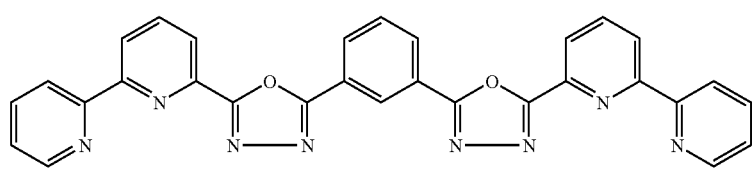

(2)

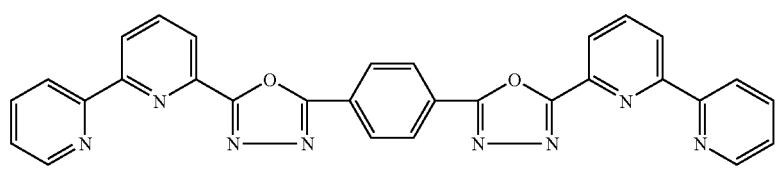

(3)

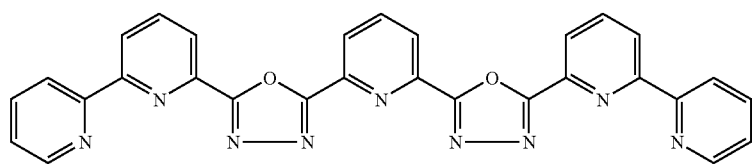

(4)

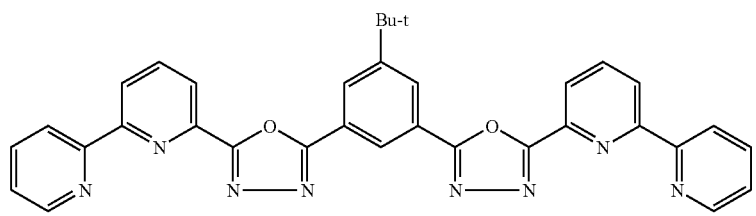

(5)

(6)
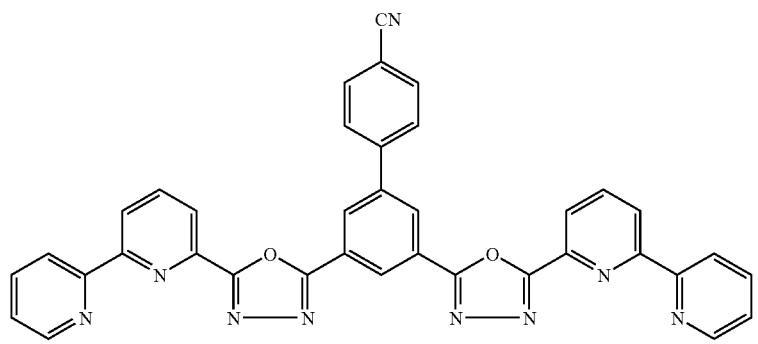
(7)
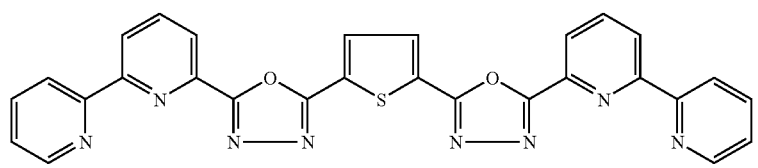
(8)
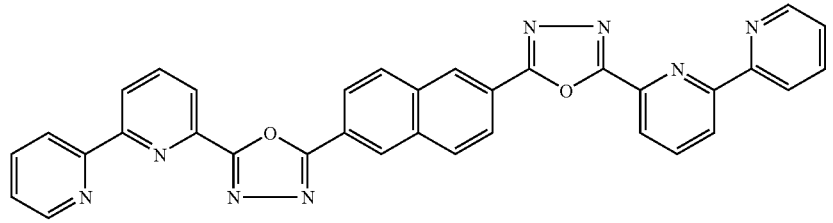
(9)
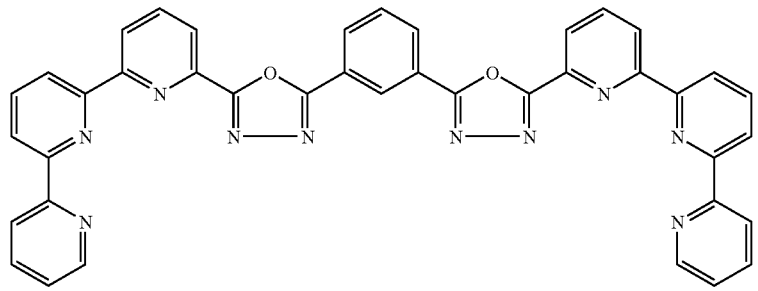
(10)
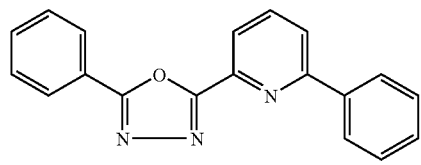
(11)
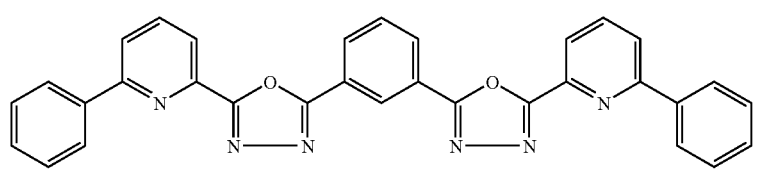

-continued

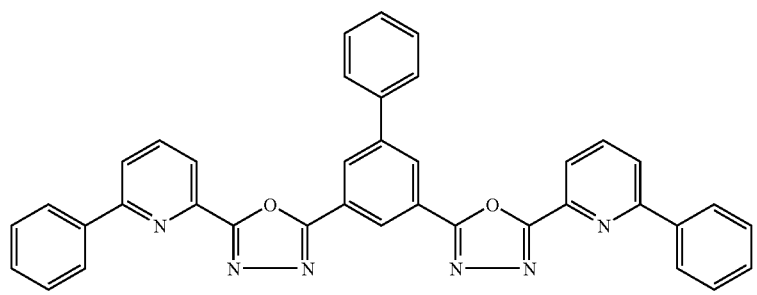
(12)

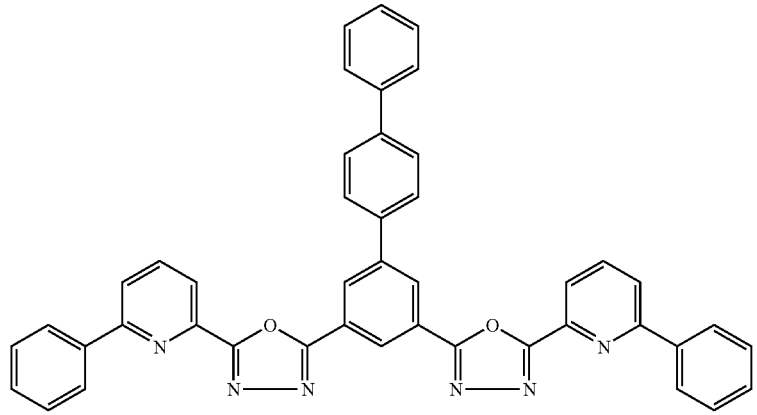
(13)

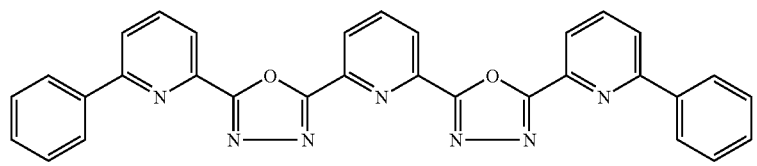
(14)

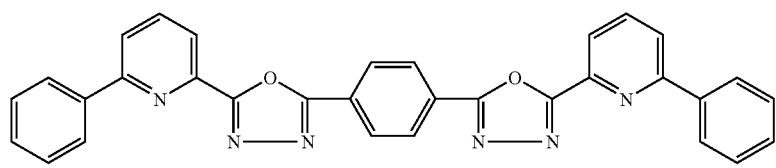
(15)

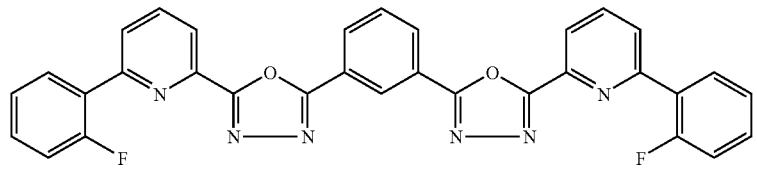
(16)

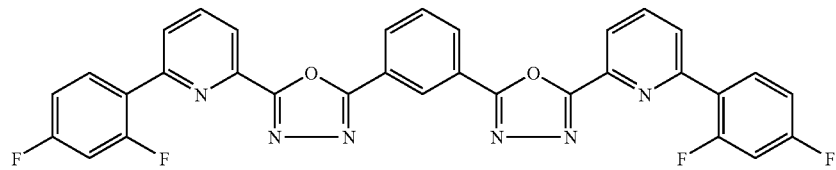
(17)

Purification of those compounds was conducted by purification with column chromatography, adsorption purification, recrystallization or crystallization with a solvent, and the like. Identification of the compound was conducted by NMR analysis. As physical property values, DSC measurement (Tg) and measurement of a melting point were conducted. A melting point serves as a measure of deposition property, and a glass transition point (Tg) serves as a measure of stability in a thin film state.

The melting point and glass transition point were measured using a powder with a sensitive differential scanning calorimeter DSC 3100S, a product of Bruker AXS.

Further, work function was measured by preparing a 100 nm thin film on an ITO substrate and using an atmospheric photoelectron spectrometer AC2, a product of Riken Keiki Co., Ltd. The work function serves as a measure of hole blocking ability.

As the structure of the organic EL device of the present invention, there are a structure comprising, successively on a substrate, an anode, a hole injecting layer, a hole transporting layer, an emission layer, a hole blocking layer, an electron transporting layer and a cathode, and the structure having an electron injecting layer between the electron transporting layer and the cathode. In those multilayered structures, several organic layers can be omitted, and for example, the structure can comprise, successively on a substrate, an anode, a hole transporting layer, an emission layer, an electron transporting layer and a cathode.

As the anode of the organic EL device, an electrode material having large work function, such as ITO or gold, is used. As the hole injecting layer, in addition to copper phthalocyanine (hereinafter referred to as CuPc), starburst type materials such as triphenyl amine derivatives and naphthalene amine compounds and coating type materials can be used.

As the hole transporting layer, benzidine derivatives such as N,N'-diphenyl-N,N'-di(m-tolyl)benzidine (hereinafter referred to as TPD) and N,N'-diphenyl-N,N'-di(α-naphthyl) benzidine (hereinafter referred to as NPD), various triphenylamine tetramers, and the like can be used. Further, as the hole injecting and transporting layer, a coating type polymer material such as PEDOT/PSS can be used.

As the emission layer, hole blocking layer and electron transporting layer of the organic EL device of the present invention, aluminum complexes, oxazole derivatives, carbazole derivatives, polydialkyl fluorene derivatives and the like can be used, in addition to the compound having an oxadiazole ring structure having a substituted pyridyl group connected thereto.

By using the conventional luminous material such as aluminum complexes and styryl derivatives in the emission layer and using the compound having an oxadiazole ring structure having a substituted pyridyl group connected thereto as the hole blocking layer and the electron transporting layer, an organic EL device of high performance can be produced. Further, by adding a dopant which is a fluorescent substance such as quinacridone, coumarin and rubrene, or a phosphorescent substance such as iridium complex of phenylpyridine, with host materials of the emission layer, an organic EL device of high performance can also be produced.

Further, the conventional electron transporting material can be laminated or co-deposited on the compound having an oxadiazole ring structure having a substituted pyridyl group connected thereto, thereby using the same as an electron transporting layer.

The organic EL device of the present invention may have an electron injecting layer. As the electron injecting layer, lithium fluoride and the like can be used. As the cathode, an electrode material having low work function such as aluminum, or an alloy having further low work function such as aluminum magnesium, is used as an electrode material.

EXAMPLES

The embodiments of the present invention are specifically illustrated with reference to the following Examples, but the invention is not limited thereto so long as not exceeding its gist.

Example 1

Synthesis of 1,3-bis[2-(2,2'-bipyridin-6-yl)-1,3,4-oxadiazol-5-yl]benzene (hereinafter referred to as BpyOXDm) (2)

0.63 g of 6-(2H-tetrazol-5-yl)-2,2'-bipyridine was dissolved in 10 ml of dehydrated pyridine, and 0.29 g of isophthaloyl dichloride was gradually added. Temperature was elevated to 115° C., and stirring was conducted for 6 hours under reflux. After cooling to room temperature, the reaction solution was poured into water, and a precipitated white solid was taken out by suction filtration, and washed with water. The solid obtained was vacuum dried at 80° C. for 20 hours, and purified with column chromatography (carrier: silica gel, eluting solution: chloroform/methanol=20/1) to obtain 0.62 g (yield 81%) of BpyOXDm. The product was identified with NMR analysis. The result of NMR analysis (CDCl3) was as follows. 9.071 ppm (1H), 8.639-8.714 ppm (6H), 8.325-8.477 ppm (4H), 8.037 ppm (2H), 7.756-7.854 ppm (3H), 7.330 ppm (2H).

Example 2

Synthesis of 1,4-bis[2-(2,2'-bipyridin-6-yl)-1,3,4-oxadiazol-5-yl]benzene (hereinafter referred to as BpyOXDp) (3)

0.67 g of 6-(2H-tetrazol-5-yl)-2,2'-bipyridine was dissolved in 10 ml of dehydrated pyridine, and 0.32 g of terephthaloyl dichloride was added. Temperature was elevated to 110° C., and stirring was conducted for 5 hours under reflux. After cooling to room temperature, the reaction solution was poured into water, and a precipitated white solid was taken out by suction filtration, and washed with water. The solid was vacuum dried at 80° C. for 20 hours to obtain a while crude product. By purifying with column chromatography, 0.58 g (yield 74%) of BpyOXDp was obtained. The product was identified with NMR analysis. The result of NMR analysis (CDCl3) was as follows. 8.736 ppm (2H), 8.640 ppm (4H), 8.463 ppm (3H), 8.260-8.384 ppm (4H), 8.060 ppm (2H), 7.932 ppm (2H), 7.380 ppm (1H).

Example 3

Synthesis of 2,6-bis[2-(2,2'-bipyridin-6-yl)-1,3,4-oxadiazol-5-yl]benzene (hereinafter referred to as BpyOXDPy) (4)

0.50 g of 6-(2H-tetrazol-5-yl)-2,2'-bipyridine was dissolved in 10 ml of dehydrated pyridine, and 0.26 g of 2,6-pyridinedicarbonyl dichloride was added. Temperature was elevated to 110° C., and stirring was conducted for 9 hours under reflux. After cooling to room temperature, the reaction solution was poured into water, and a precipitated white solid was taken out by suction filtration, and washed with water. The solid was vacuum dried at 80° C. for 20 hours to obtain a while crude product. By purifying with column chromatography, 0.12 g (yield 24%) of BpyOXDPy was obtained. The product was identified with NMR analysis. The result of NMR analysis (CDCl3) was as follows. 8.005-8.648 ppm (13H), 7.667 ppm (2H), 7.256 ppm (2H).

Example 4

Synthesis of 5-tertiary butyl(1,3-bis[2-(2,2'-bipyridin-6-yl)-1,3,4-oxadiazol-5-yl]benzene (hereinafter referred to as BpyOXDm(5tBu) (5)

5.00 g of 6-(2H-tertazol-5-yl)-2,2'-bipyridine was dissolved in 100 ml of pyridine, and dehydrated by azeotropy. 3.06 g of 5-tertiary butyl isophthaloyl dichloride was added.

Temperature was elevated to 110° C., and stirring was conducted for 1 hour under reflux. After cooling to room temperature, the reaction solution was poured into water, and a sodium hydroxide aqueous solution was added. A precipitated solid was taken out by suction filtration, and washed with water. The solid was dried at 80° C. under reduced pressure to obtain 5.46 g (yield 84%) of BpyOXDm(5tBu). The product was identified with NMR analysis. The result of NMR analysis (CDCl3) was as follows. 8.852-8.863 ppm (1H), 8.636-8.723 ppm (6H), 8.489-8.495 ppm (2H), 8.339-8.371 ppm (2H), 8.014-8.086 ppm (2H), 7.764-7.828 ppm (2H), 7.307-7.357 ppm (2H), 1.526 ppm (9H).

Example 5

Synthesis of 3,5-bis[2-(2,2'-bipyridin-6-yl)-1,3,4-oxadiazol-5-yl]-4'-cyano-1,1'-biphenyl (hereinafter referred to as CPBO) (6)

4.9 g of 3,5-bis[2-(2-phenylpyridin-6-yl)-1,3,4-oxadiazol-5-yl]-1-bromobenzene was added to 1,200 ml of dehydrated toluene and 200 ml of ethanol, and 1.79 g of 4-cyanophenylboric acid, 186 mg of tetrakis(triphenylphosphine)palladium and 3.73 g of cesium fluoride were added. Temperature was elevated to 75° C., and stirring was conducted for 20 hours. After cooling to room temperature, the reaction solvent was distilled off under reduced pressure, and 300 ml of chloroform was introduced, followed by water washing. After drying an organic layer with magnesium sulfate, a solvent was distilled off under reduced pressure. A solid obtained was purified by dispersion washing with toluene-methanol (4:1) to obtain 3.17 g (yield 62%) of CPBO. The product was identified with NMR analysis. The result of NMR analysis (CDCl3) was as follows. 9.12 ppm (1H), 8.63-8.74 ppm (8H), 8.39 ppm (2H), 8.08 ppm (2H), 7.78-7.95 ppm (6H), 7.33-7.38 ppm (2H).

Example 6

Synthesis of 2,5-bis[2-(2,2'-bipyridin-6-yl)-1,3,4-oxadiazol-5-yl]thiophene (hereinafter referred to as BpyOXDTh) (7)

5.00 g of 6-(2H-tetrazol-5-yl)-2,2'-bipyridine was dissolved in 100 ml of pyridine, and dehydrated by azeotropy. 2.47 g of 2,5-thiophenedicarbonyl dichloride was added. Temperature was elevated to 110° C., and stirring was conducted for 1 hour under reflux. After cooling to room temperature, the reaction solution was poured into water, and a sodium hydroxide aqueous solution was added. A precipitated solid was taken out by suction filtration, and washed with water. The solid was dried at 70° C. under reduced pressure to obtain a yellow crude product. The product was washed with toluene and then dried at 70° C. under reduced pressure to obtain 4.62 g (yield 78%) of BpyOXDTh. The product was identified with NMR analysis. The result of NMR analysis (CDCl3) was as follows. 8.619-8.733 ppm (6H), 8.307-8.335 ppm (2H), 7.887-8.071 ppm (6H), 7.370-7.441 ppm (2H).

Example 7

Synthesis of 2,6-bis[2-(2,2'-bipyridin-6-yl)-1,3,4-oxadiazol-5-yl]naphthalene (hereinafter referred to as BpyOXD(2,6NP)) (8)

5.00 g of 6-(2H-tetrazol-5-yl)-2,2'-bipyridine was dissolved in 100 ml of pyridine, and dehydrated by azeotropy. 2.99 g of 2,6-naphthalenedicarbonyl dichloride was added. Temperature was elevated to 110° C., and stirring was conducted for 1 hour under reflux. After cooling to room temperature, the reaction solution was poured into water, and a sodium hydroxide aqueous solution was added. A precipitated solid was taken out by suction filtration, and washed with water. The solid was dried at 70° C. under reduced pressure to obtain 5.41 g (yield 84%) of a pale grayish brown BpyOXD(2,6NP). The product was identified with NMR analysis. The result of NMR analysis (CDCl3) was as follows. 8.837 ppm (2H), 8.642-8.754 ppm (6H), 8.360-8.452 ppm (4H), 8.205-8.237 ppm (2H), 7.923-8.094 ppm (4H), 7.386-7.430 (2H).

Example 8

Synthesis of 1,3-bis[2-(2,2':6'2''-terpyridin-6-yl)-1,3,4-oxadiazol-5-yl]benzene (hereinafter referred to as TpyOXDm) (9)

2.0 g of 6-(2H-tetrazol-5-yl)-2,2':6'2''-terpyridine was dissolved in 50 ml of dehydrated pyridine. Temperature was elevated to 120° C., and 30 ml was dehydrated by azeotropy. After cooling to 50° C., 0.68 g of isophthaloyl dichloride was added. Temperature was elevated to 110° C., and stirring was conducted for 3 hours under flux. After cooling to room temperature, the reaction solution was poured into 200 ml water, and a precipitated yellowish-brown solid was taken out by suction filtration, and washed with water. The solid obtained was vacuum dried at 80° C. for 20 hours, and purified with adsorption purification (carrier: NH silica gel, eluting solution: chloroform) to obtain 1.53 g (yield 67%) of TpyOXDm. The product was identified with NMR analysis. The result of NMR analysis (CDCl3) was as follows. 9.12 ppm (1H), 8.85 ppm (2H), 8.62-8.73 ppm (6H), 8.37-8.51 ppm (6H), 7.79-8.12 ppm (7H), 7.35 ppm (2H).

Example 9

Synthesis of 5-phenyl-2-(2-phenylpyridin-6-yl)-1,3,4-oxadiazole (hereinafter referred to as PhpyOXDPh) (10)

5.0 g of 2-phenyl-6-(2H-tetrazol-5-yl)pyridine was dissolved in 125 ml of dehydrated pyridine. Temperature was elevated to 120° C., and 75 ml was dehydrated by azeotropy. After cooling to 50° C., 3.17 g of benzoyl chloride was added. Temperature was elevated to 100° C., and stirring was conducted for 2 hours under flux. After cooling to room temperature, the reaction solution was poured into 300 ml water, and after adjusting pH to 12 with 20% sodium hydroxide aqueous solution, stirring was conducted for 1 hour. A precipitated yellow solid was taken out by suction filtration, and washed with water. The solid obtained was vacuum dried at 70° C. for 20 hours, and purified with adsorption purification (carrier: NH silica gel, eluting solution: chloroform) to obtain 6.11 g (yield 91%) of PhpyOXDPh. The product was identified with NMR analysis. The result of NMR analysis (CDCl3) was as follows. 8.23-8.26 ppm (3H), 8.14-8.17 ppm (2H), 7.90-7.99 ppm (2H), 7.48-7.58 ppm (6H).

Example 10

Synthesis of 1,3-bis[2-(2-phenylpyridin-6-yl)-1,3,4-oxadiazol-5-yl]benzene (hereinafter referred to as PhpyOXDm) (11)

5.0 g of 2-phenyl-6-(2H-tetrazol-5-yl)pyridine was dissolved in 125 ml of dehydrated pyridine. Temperature was elevated to 120° C., and 75 ml was dehydrated by azeotropy. After cooling to 50° C., 2.28 g of isophthaloyl dichloride was added. Temperature was elevated to 100° C., and stirring was conducted for 1 hour. After cooling to room temperature, the reaction solution was poured into 300 ml water, and after adjusting pH to 12 with 20% sodium hydroxide aqueous solution, stirring was conducted for 1 hour. A precipitated brown solid was taken out by suction filtration, and washed with water. The solid obtained was vacuum dried at 70° C. for 20 hours, and purified with column chromatography (carrier: NH silica gel, eluting solution: chloroform) to obtain 4.27 g (yield 73%) of PhpyOXDm. The product was identified with NMR analysis. The result of NMR analysis (CDCl3) was as follows. 9.07 ppm (1H), 8.46 ppm (2H), 8.28 ppm (2H), 8.17 ppm (4H), 7.92-8.15 ppm (4H), 7.78 ppm (1H), 7.46-7.55 ppm (6H).

Example 11

Synthesis of 3,5-bis[2-(2-phenylpyridin-6-yl)-1,3,4-oxadiazol-5-yl]-1,1'-biphenyl (hereinafter referred to as PhpyOXDBP) (12)

2.4 g of 3,5-bis[2-(2-phenylpyridin-6-yl)-1,3,4-oxadiazol-5-yl]-1-bromobenzene was added to 960 ml of deaerated toluene and 240 ml of ethanol, and 40 ml of 2M-potassium carbonate aqueous solution, 144 mg of tetrakis(triphenylphosphine)palladium and 586 mg of phenylboric acid were added. Temperature was elevated to 80° C., and stirring was conducted for 20 hours. After cooling to room temperature, the reaction solvent was distilled off under reduced pressure, and 300 ml of chloroform was introduced, followed by water washing. After drying an organic layer with magnesium sulfate, a solvent was distilled off under reduced pressure. A solid obtained was purified with column chromatography (carrier: silica gel, eluting solution: chloroform) to obtain 1.86 g (yield 78%) of PhpyOXDBP. The product was identified with NMR analysis. The result of NMR analysis (CDCl3) was as follows. 9.02 ppm (1H), 8.65 ppm (2H), 8.29 ppm (2H), 8.15 ppm (4H), 7.92-8.03 ppm (4H), 7.79 ppm (2H), 7.45-7.56 ppm (9H).

Example 12

Synthesis of 3,5-bis[2-(2-phenylpyridin-6-yl)-1,3,4-oxadiazol-5-yl]-1,1':4'1"-terphenyl (hereinafter referred to as PhpyOXDTP) (13)

2.5 g of 3,5-bis[2-(2-phenylpyridin-6-yl)-1,3,4-oxadiazol-5-yl]-1-bromobenzene was added to 1,000 ml of deaerated toluene and 250 ml of ethanol, and 42 ml of 2M-potassium carbonate aqueous solution, 145 mg of tetrakis(triphenylphosphine)palladium and 991 mg of 4-biphenylboric acid were added. Temperature was elevated to 80° C., and stirring was conducted for 20 hours. After cooling to room temperature, the reaction solvent was distilled off under reduced pressure, and 600 ml of chloroform was introduced, followed by water washing. After drying an organic layer with magnesium sulfate, a solvent was distilled off under reduced pressure. A solid obtained was purified with adsorption purification (carrier: NH silica gel, eluting solution: chloroform) to obtain 2.13 g (yield 76%) of PhpyOXDTP. The product was identified with NMR analysis. The result of NMR analysis (CDCl3) was as follows. 9.03 ppm (1H), 8.71 ppm (2H), 8.30 ppm (2H), 8.16 ppm (4H), 7.68-8.03 ppm (10H), 7.40-7.52 ppm (9H).

Example 13

Synthesis of 2,6-bis[2-(2-phenylpyridin-6-yl)-1,3,4-oxadiazol-5-yl]pyridine (hereinafter referred to as PhpyOXDPy) (14)

5.0 g of 2-phenyl-6-(2H-tetrazol-5-yl)pyridine was dissolved in 125 ml of dehydrated pyridine, and dehydrated by 75 ml by azeotropy by heating to 120° C. After cooling to 50° C., 2.30 g of 2,6-pyridinedicarbonyl dichloride was added. Temperature was elevated to 100° C., and stirring was conducted for 2 hours. After cooling to room temperature, the reaction solution was poured into 300 ml of water, and pH was adjusted by 12 with a 20% sodium hydroxide aqueous solution, followed by stirring for 1 hour. A precipitated dark greenish black solid was taken out by suction filtration, and washed with water. The solid was vacuum dried at 70° C. for 20 hours. The solid obtained was purified with column chromatography (carrier: silica gel, eluting solution: chloroform) to obtain 3.95 g (yield 67%) of PhpyOXDPy. The product was identified with NMR analysis. The result of NMR analysis (CDCl3) was as follows. 8.54 ppm (2H), 8.30 ppm (2H), 8.14-8.20 ppm (5H), 7.94-8.01 ppm (4H), 7.41-7.51 ppm (6H).

Example 14

Synthesis of 1,4-bis[2-(2-phenylpyridin-6-yl)-1,3,4-oxadiazol-5-yl]benzene (hereinafter referred to as PhpyOXDp) (15)

5.0 g of 2-phenyl-6-(2H-tetrazol-5-yl)pyridine was dissolved in 125 ml of dehydrated pyridine. Temperature was elevated to 120° C., and 75 ml was dehydrated by azeotropy. After cooling to 50° C., 2.30 g of terephthaloyl dichloride was added. Temperature was elevated to 100° C., and stirring was conducted for 5 hours. After cooling to room temperature, the reaction solution was poured into 300 ml water, and after adjusting pH to 12 with 20% sodium hydroxide aqueous solution, stirring was conducted for 1 hour. A precipitated yellow solid was taken out by suction filtration, and washed with water. The solid obtained was vacuum dried at 70° C. for 20 hours, and purified with dispersion washing by a chloroform-methanol mixed solution to obtain 3.40 g (yield 58%) of PhpyOXDp. The product was identified with NMR analysis. The result of NMR analysis (CDCl3) was as follows. 8.45 ppm (4H), 8.29 ppm (2H), 8.16 ppm (4H), 7.93-8.02 ppm (4H), 7.50-7.59 ppm (6H).

Example 15

Synthesis of 1,3-bis[(2-(2'-fluorophenyl)pyridin-6-yl)-1,3,4-oxadiazol-5-yl]benzene (hereinafter referred to as FPhpyOXDm) (16)

3.0 g of 2-(2-fluorophenyl)-6-(2H-tetrazol-5-yl)-pyridine was dissolved in 125 ml of dehydrated pyridine. Temperature was elevated to 120° C., and 75 ml was dehydrated by azeotropy. After cooling to 50° C., 1.30 g of isophthaloyl dichloride was added. Temperature was elevated to 100° C., and stirring was conducted for 1 hour. After cooling to room temperature, the reaction solution was poured into 300 ml water, and after adjusting pH to 12 with 20% sodium hydroxide aqueous solution, stirring was conducted for 1 hour. A precipitated yellow solid was taken out by suction filtration, and washed with water. The solid obtained was vacuum dried at 70° C. for 20 hours, and purified with adsorption purification (carrier: NH silica gel, eluting solution: chloroform) to obtain 2.21 g (yield 63%) of FPhpyOXDm. The product was identified with NMR analysis. The result of NMR analysis (CDCl3) was as follows. 9.05 ppm (1H), 8.44 ppm (2H), 8.30 ppm (2H), 8.22 ppm (2H), 7.96-8.05 ppm (4H), 7.77 ppm (1H), 7.16-7.48 ppm (6H).

Example 16

Synthesis of 1,3-bis[(2-(2',4'-difluorophenyl)pyridin-6-yl)-1,3,4-oxadiazol-5-yl]benzene (hereinafter referred to as DFPhpyOXDm) (17)

3.0 g of 2-(2,4-difluorophenyl)-6-(2H-tetrazol-5-yl)-pyridine was dissolved in 125 ml of dehydrated pyridine. Temperature was elevated to 120° C., and 75 ml was dehydrated by azeotropy. After cooling to 50° C., 1.20 g of isophthaloyl dichloride was added. Temperature was elevated to 100° C., and stirring was conducted for 1 hour. After cooling to room temperature, the reaction solution was poured into 300 ml water, and after adjusting pH to 12 with 20% sodium hydroxide aqueous solution, stirring was conducted for 1 hour. A precipitated brown solid was taken out by suction filtration, and washed with water. The solid obtained was vacuum dried at 70° C. for 20 hours, and purified with adsorption purification (carrier: NH silica gel, eluting solution: chloroform) to obtain 2.79 g (yield 81%) of DFPhpyOXDm. The product was identified with NMR analysis. The result of NMR analysis (CDCl3) was as follows. 9.05 ppm (1H), 8.45 ppm (2H), 8.21-8.31 ppm (4H), 7.98-8.01 ppm (4H), 7.79 ppm (1H), 6.92-7.09 ppm (4H).

Example 17

Regarding the compounds of the present invention, a melting point and a glass transition point were obtained by a sensitive differential scanning calorimeter (a product of Bruker AXS, DSC 3100S).

|  | Melting point | Glass transition point |
|---|---|---|
| BpyOXDm | 243° C. | 106° C. |
| BpyOXDPy | 253° C. | 114° C. |
| BpyOXDm (5tBu) | 274° C. | 105° C. |
| CPBO | 341° C. | 136° C. |
| TpyOXDm | 276° C. | 119° C. |
| PhpyOXDBP | 262° C. | 101° C. |
| PhpyOXDTP | 285° C. | 116° C. |

The compounds of the present invention have high glass transition point and are stable in a thin film form.

Example 18

A deposition film having a thickness of 100 nm was formed on an ITO substrate using the compound of the present invention, and work function was measured with an atmospheric photoelectron spectrometer (AC2, a product of Riken Keiki Co., Ltd.). The compounds of the present invention all had a value exceeding 6.2 eV which is the measurement limit of a measurement apparatus.

Thus, the compound of the present invention apparently has the work function larger than the hole transporting material, and has large hole blocking ability.

Example 19

As shown in FIG. 1, an organic EL device was prepared by depositing a hole transporting layer 4, an emission layer 5, an electron transporting layer 7 and a cathode (aluminum magnesium electrode) 9 successively on an ITO electrode as a transparent anode 2 previously formed on a glass substrate 1. The glass substrate 1 having formed thereon ITO having a film thickness of 150 nm formed thereon was washed with an organic solvent, and the surface thereof was washed with oxygen plasma treatment. This was fitted in a vacuum deposition machine, and pressure was reduced to 0.001 Pa or lower.

Subsequently, as the hole transporting layer 4, TPD was formed in about 50 nm at a deposition rate of 6 nm/min. Next, as the emission layer 5, Alq was formed in about 20 nm at a deposition rate of 6 nm/min. On this emission layer 5, as the electron transporting layer 7, BpyOXDm (2) was formed in about 30 nm at a deposition rate of 6 nm/min. The above depositions each were continuously conducted without breaking vacuum. Finally, a mask for cathode deposition was inserted, and an alloy of MgAg was deposited in about 200 nm at a ratio of 10:1 to form the cathode 9. The device prepared was stored in a vacuum desciccator, and characteristic measurement was conducted at ordinary temperature in atmosphere.

Characteristics of the organic EL device of the present invention thus formed were evaluated by voltage applied at which emission of 100 cd/m$^2$ is obtained, emission luminance in the case of loading a current density of 200 mA/cm$^2$, and emission efficiency defined by emission luminance/voltage.

As a result of applying a direct current voltage to the organic EL device, emission of 100 cd/m$^2$ was observed from 3.7 V. At 7.8 V, current of 200 mA/cm$^2$ flowed, and a stable green emission of 11,900 cd/m$^2$ was obtained. The emission efficiency at this luminance was high efficiency of 6.0 cd/A.

Example 20

An organic EL device was prepared under the same conditions as in Example 19, except that in the device of FIG. 1, the material of the electron transporting layer 7 was changed from BpyOXDm (2) to BpyOXDPy (4), and the characteristics were examined. Emission of 100 cd/m$^2$ was observed from 4.0 V. At 8.5 V, current of 200 mA/cm$^2$ flowed, and a stable green emission of 11,500 cd/m$^2$ was obtained. The emission efficiency at this luminance was high efficiency of 5.8 cd/A.

Comparative Example 1

For the sake of comparison, an organic EL device was prepared under the same conditions as in Example 19, except that the material of the electron transporting layer 7 was changed to Alq, and the characteristics were examined. That is, as a layer serving as both emission layer 5 and electron transporting layer 7, Alq3 was formed in about 50 nm at a deposition rate of 6 nm/min. Emission of 100 cd/m$^2$ was observed from 7.2 V. At 13.3 V, current of 200 mA/cm² flowed, and a green emission of 9,600 cd/m² was obtained. The emission efficiency at this luminance was 4.6 cd/A.

Thus, the organic EL device of the present invention is excellent in emission efficiency as compared with the device using Alq used as the general electron transporting material, and can achieve remarkable reduction in driving voltage. Therefore, it was understood to be excellent in durability.

From that apparent reduction in driving voltage was recognized in the above comparative test, it is predicted that the electron mobility of the compound of the present invention is far higher than Alq which is the conventional electron transporting material.

Example 21

Figure 2:
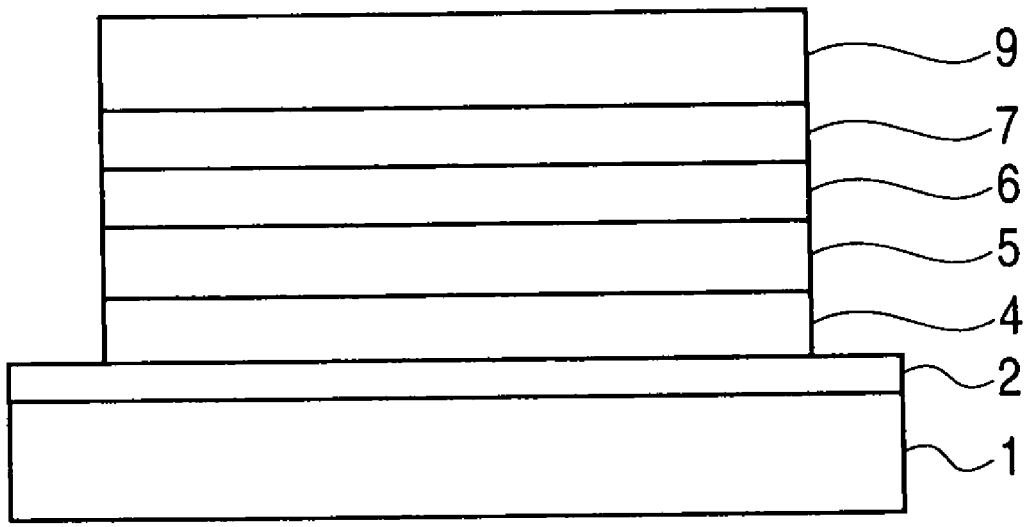
FIG. 2 is a view showing an EL device structure of Example 21.

An organic EL device as shown in FIG. 2 was prepared by depositing a hole transporting layer 4, an emission layer 5, a hole blocking layer 6, an electron transporting layer 7 and a cathode (aluminum magnesium electrode) 9 successively on an ITO electrode as a transparent anode 2 previously formed on a glass substrate 1. The glass substrate 1 having formed thereon ITO having a film thickness of 150 nm was washed with an organic solvent, and the surface thereof was washed with oxygen plasma treatment. This was fitted in a vacuum deposition machine, and pressure was reduced to 0.001 Pa or lower.

Subsequently, as the hole transporting layer 4, TPD was formed in about 50 nm at a deposition rate of 6 nm/min. Next, as the emission layer 5, Alq was formed in about 30 nm at a deposition rate of 6 nm/min. On this emission layer 5, as the electron inhibiting layer 6, BpyOXDm (2) was formed in about 20 nm at a deposition rate of 6 nm/min. Further, as the electron transporting layer 7, Alq was formed in about 20 nm at a deposition rate of 6 nm/min. The above depositions each were continuously conducted without breaking vacuum. Finally, a mask for cathode deposition was inserted, and an alloy of MgAg was deposited in about 200 nm at a ratio of 10:1 to form the cathode 9. The device prepared was stored in a vacuum desciccator, and characteristic measurement was conducted at ordinary temperature in atmosphere.

As a result of applying a direct current voltage to the organic EL device of the present invention thus prepared, emission of 100 cd/m² was observed from 5.7 V. At 11.4 V, current of 200 mA/cm² flowed, and a stable green emission of 11,600 cd/m² was obtained. The emission efficiency at this luminance was high efficiency of 6.0 cd/A. The applied voltage was further increased to obtain the maximum luminance before breakthrough of 22,050 cd/m². The maximum luminance measured reflects electrical stability of a device, and is therefore a measure of durability of the organic EL device.

Comparative Example 2

For the sake of comparison, an organic EL device was prepared under the same conditions as in Example 21, except that the material of the electron inhibiting layer 6 was changed to BCP, and the characteristics were examined. That is, as a hole blocking layer 6, BCP was formed in about 20 nm at a deposition rate of 6 nm/min. Emission of 100 cd/m² was observed from 12.0 V. At 19.4 V, current of 200 mA/cm² flowed, and a green emission of 10,900 cd/m² was obtained. The emission efficiency at this luminance was 5.3 cd/A. The maximum luminance before breakthrough was 12,790 cd/m².

Thus, it was understood that the organic EL device of the present invention is excellent in durability as compared with the device using BCP used as the general hole blocking material. Further, it was understood to be an organic EL device suitable to high luminance emission.

Example 22

Figure 3:
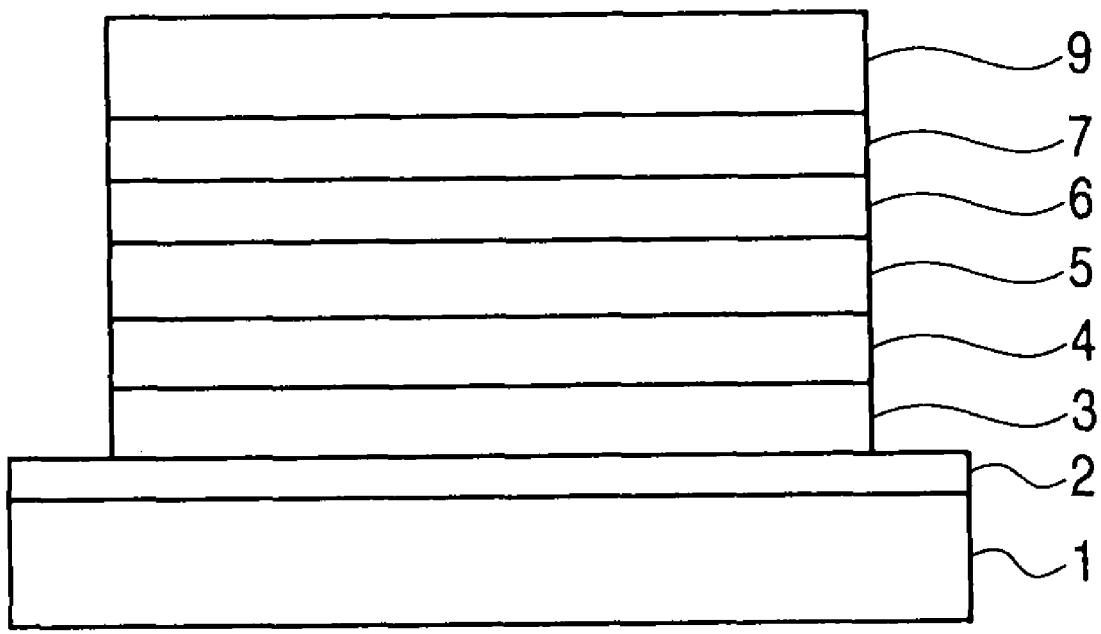
FIG. 3 is a view showing an EL device structure of Example 22.

An organic EL device as shown in FIG. 3 was prepared by depositing a hole injecting layer 3, a hole transporting layer 4, an emission layer 5, a hole blocking layer 6, an electron transporting layer 7 and a cathode (aluminum magnesium electrode) 9 successively on an ITO electrode as a transparent anode 2 previously formed on a glass substrate 1. The glass substrate 1 having formed thereon ITO having a film thickness of 150 nm was washed with an organic solvent, and the surface thereof was washed with oxygen plasma treatment. This was fitted in a vacuum deposition machine, and pressure was reduced to 0.001 Pa or lower.

Subsequently, as the hole injecting layer 3, CuPc was formed in about 15 nm at a deposition rate of 6 nm/min. On this layer, as the hole transporting layer 4, TPD was formed in about 50 nm at a deposition rate of 6 nm/min. The above depositions each were continuously conducted without breaking vacuum. A boat was exchanged, pressure was again reduced, and on the hole transporting layer 4, as the emission layer 5, Alq was formed in about 20 nm at a deposition rate of 6 nm/min. On the emission layer 5, as a layer serving as both hole blocking layer 6 and electron transporting layer 7, BpyOXDm (2) of the present invention was formed in about 30 nm at a deposition rate of 6 nm/min. Finally, pressure was returned to atmospheric pressure, a mask for cathode deposition was inserted, pressure was again reduced, and an alloy of MgAg was deposited in about 200 nm at a ratio of 10:1 to form the cathode 9. The device prepared was stored in a vacuum desciccator, and characteristic measurement was conducted at ordinary temperature in atmosphere.

As a result of applying a direct current voltage to the organic EL device of the present invention thus prepared, green light emission of 100 cd/m² was observed from 3.8 V. The maximum luminance before breakthrough of this device was 40,660 cd/m².

Comparative Example 3

For the sake of comparison, an organic EL device was prepared under the same conditions as in Example 22, except that BpyOXDm (2) of the present invention was replaced by Alq. That is, as a layer serving as all of emission layer 5, hole blocking layer 6 and electron transporting layer 7, Alq was formed in about 50 nm at a deposition rate of 6 nm/min. Green emission of 100 cd/m² was observed from 7.2 V. The maximum luminance before breakthrough was 14,990 cd/m².

Thus, it was understood that the organic EL device of the present invention is excellent in durability, and is an organic EL device suitable to high luminance emission.

Example 23

Figure 4:
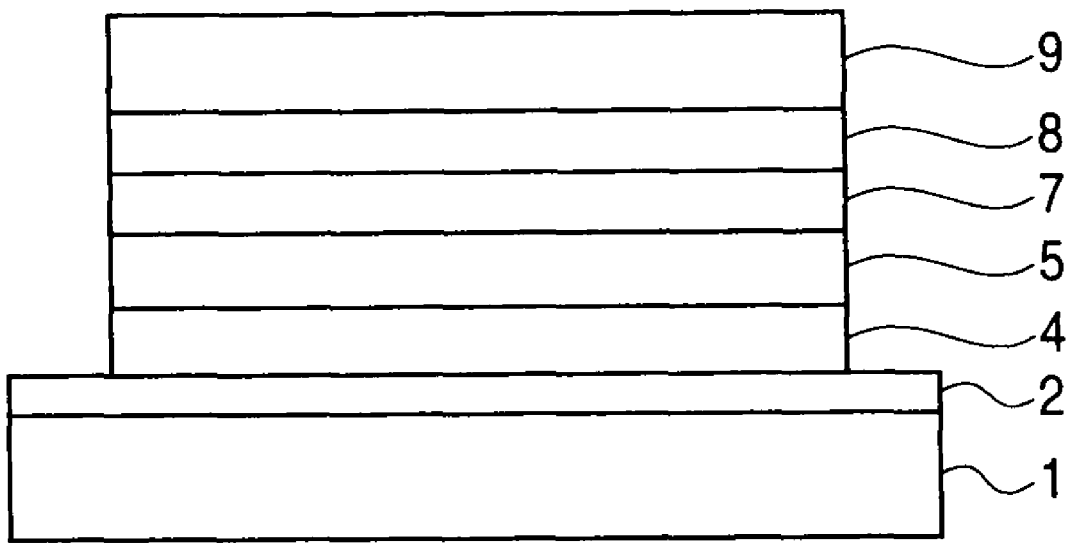
FIG. 4 is a view showing an EL device structure of Example 23.
Figure 5:
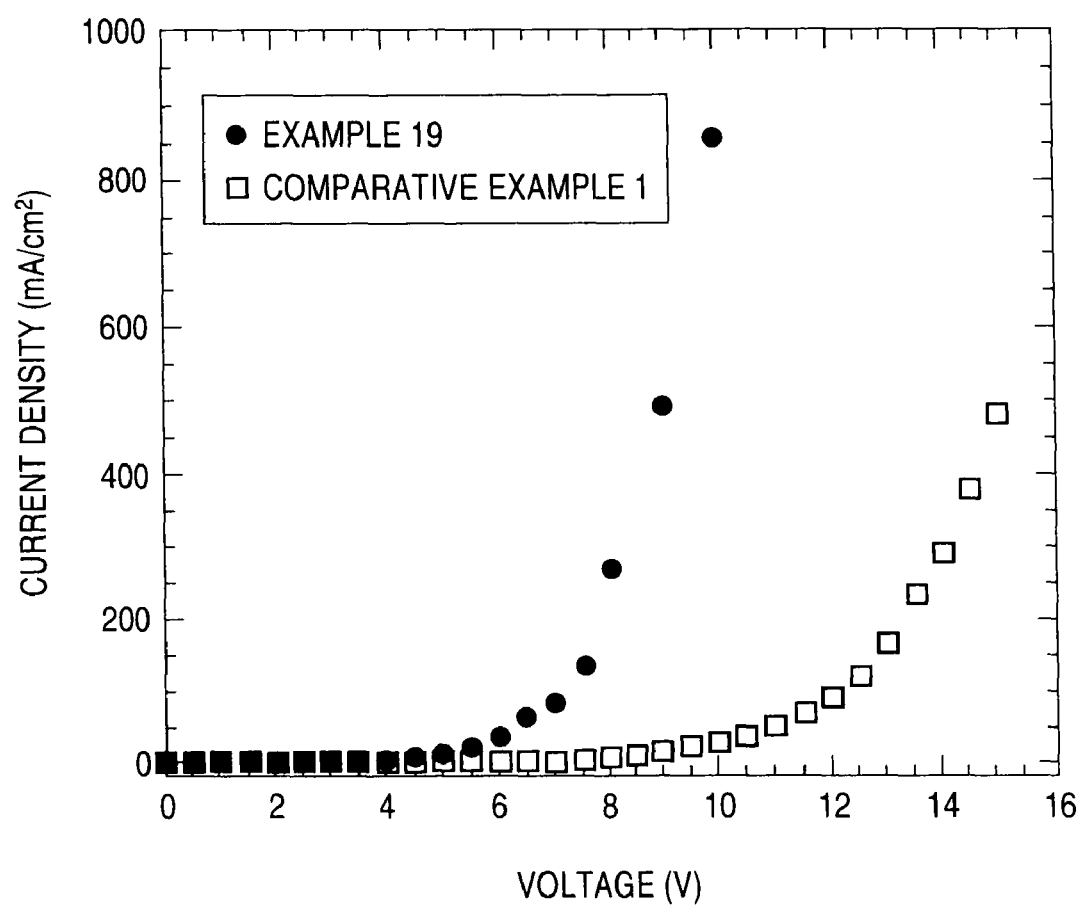
FIG. 5 is a graph comparing voltage/current density characteristics between Example 19 and Comparative Example 1.
Figure 6:
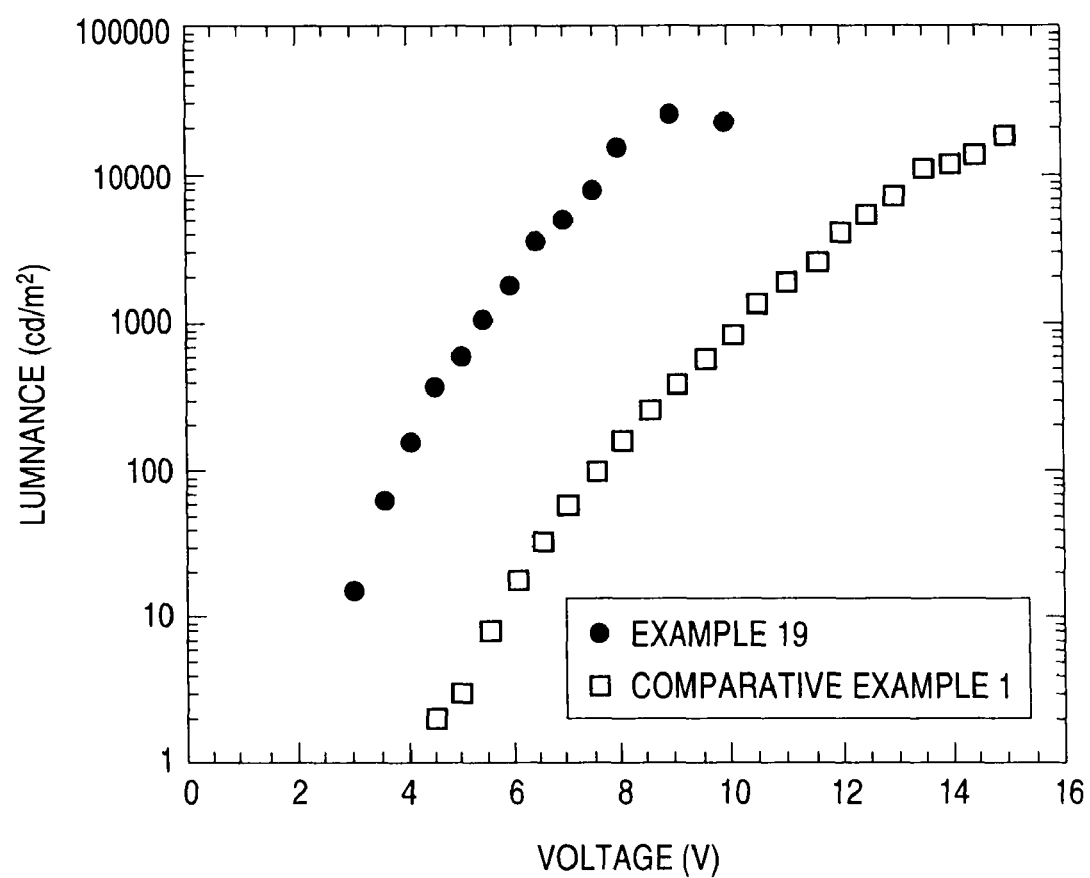
FIG. 6 is a graph comparing voltage/luminance characteristics between Example 19 and Comparative Example 1.
Figure 7:
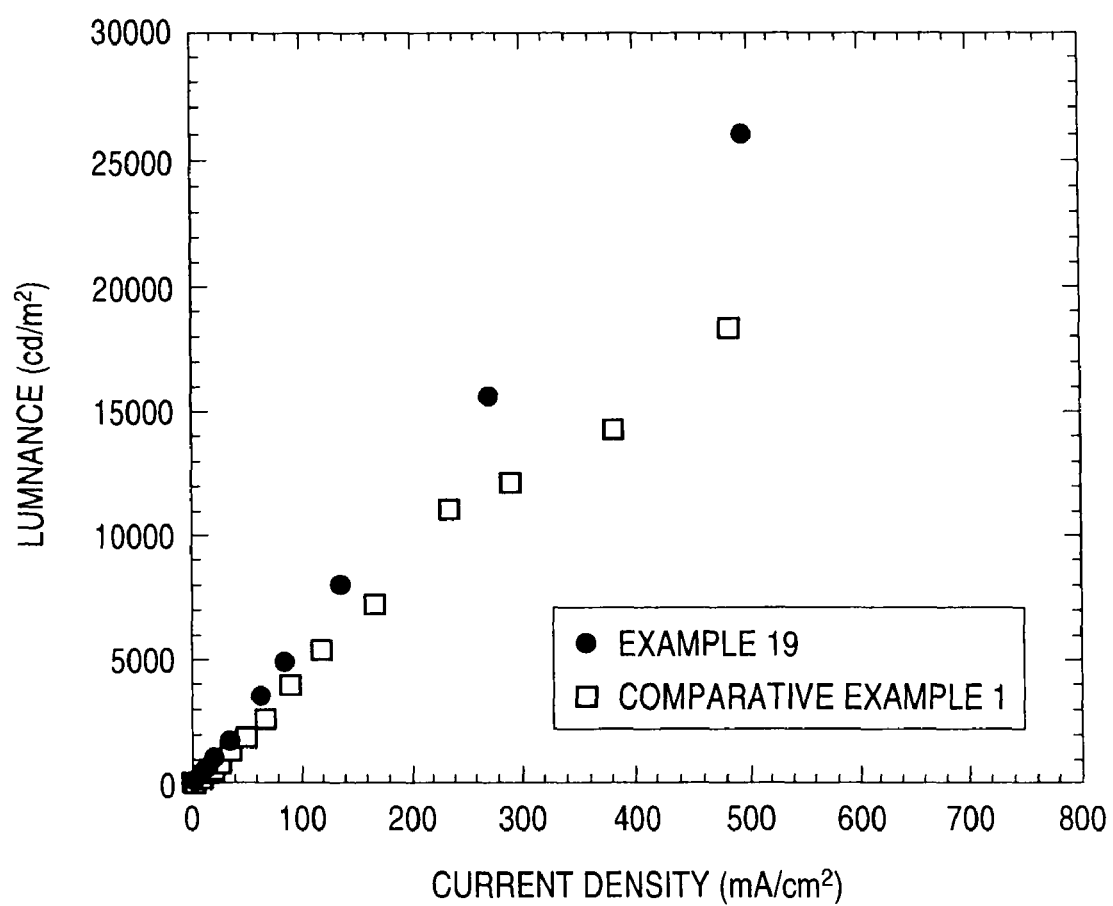
FIG. 7 is a graph comparing current density/luminance characteristics between Example 19 and Comparative Example 1.
Figure 8:
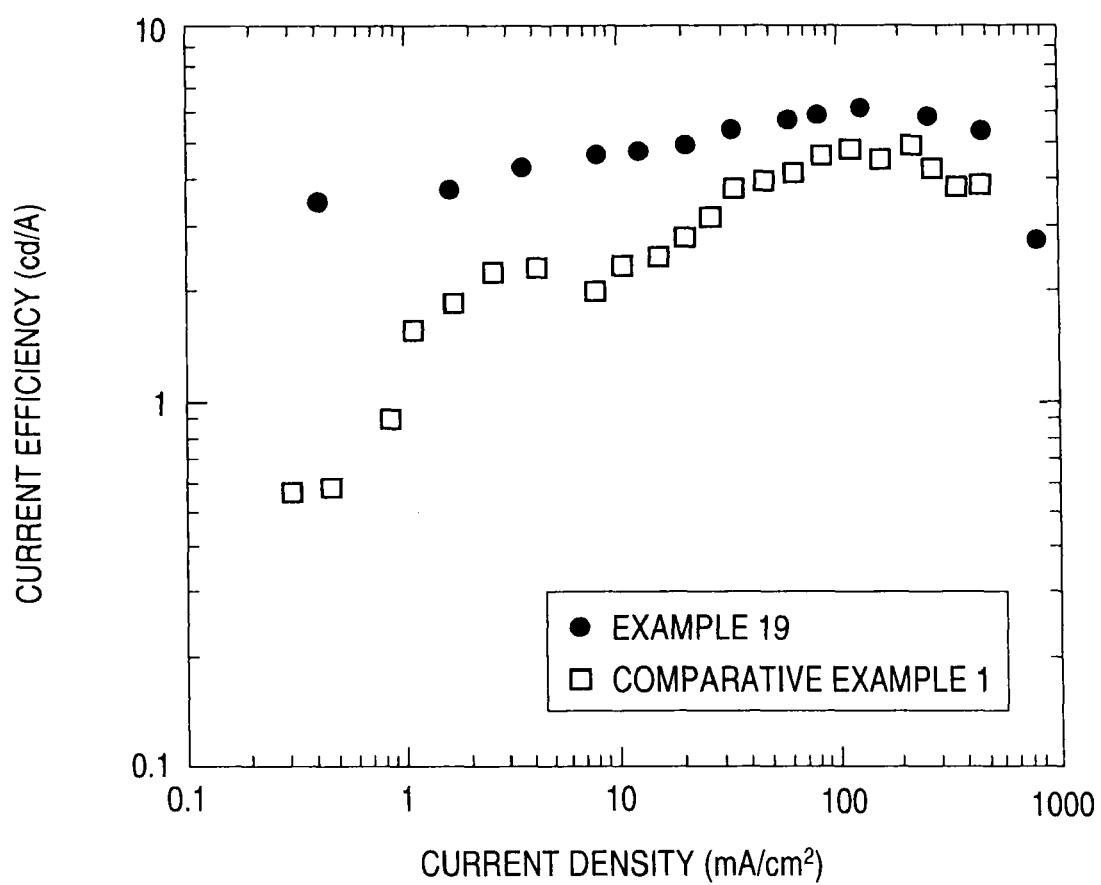
FIG. 8 is a graph comparing current density/current efficiency characteristics between Example 19 and Comparative Example 1.
Figure 9:
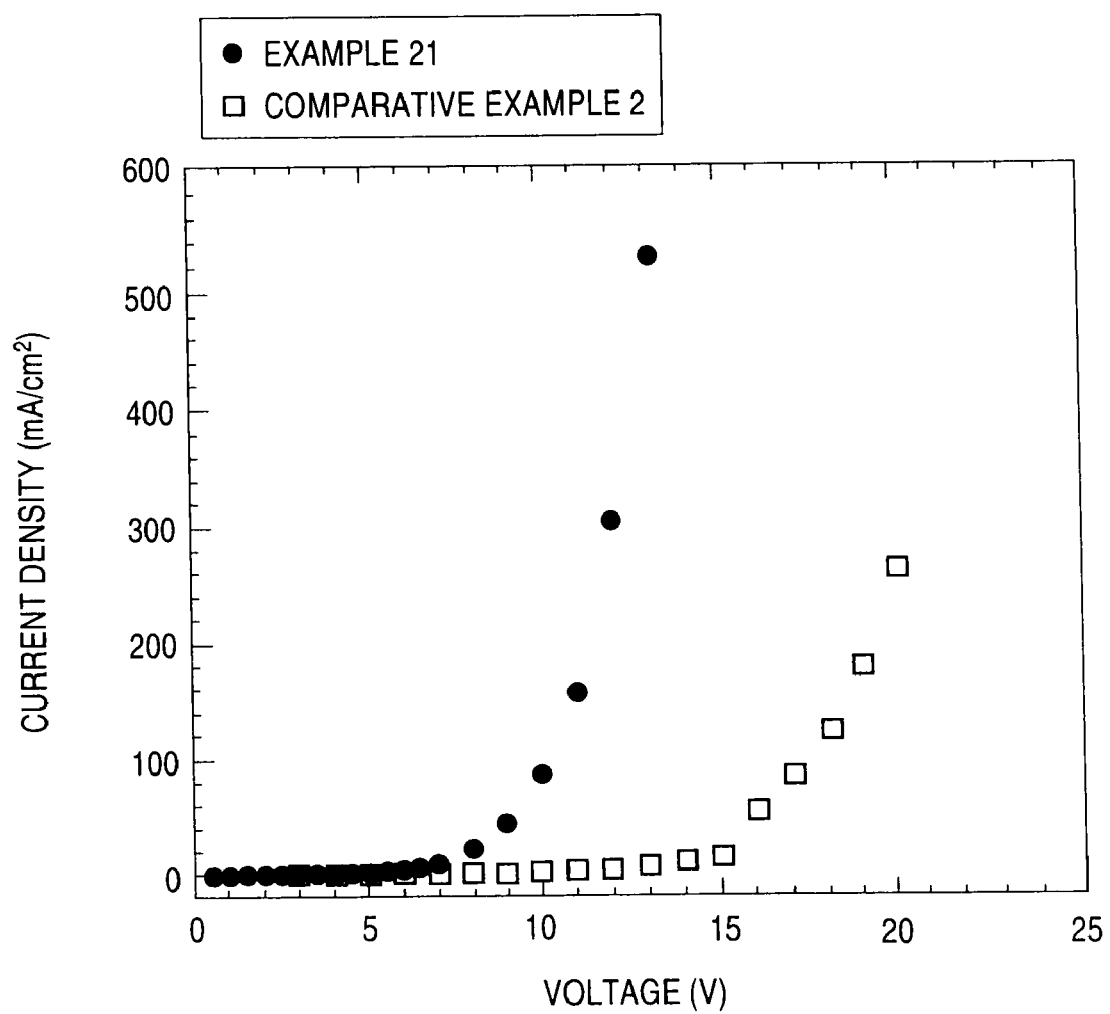
FIG. 9 is a graph comparing voltage/current density characteristics between Example 21 and Comparative Example 2.
Figure 10:
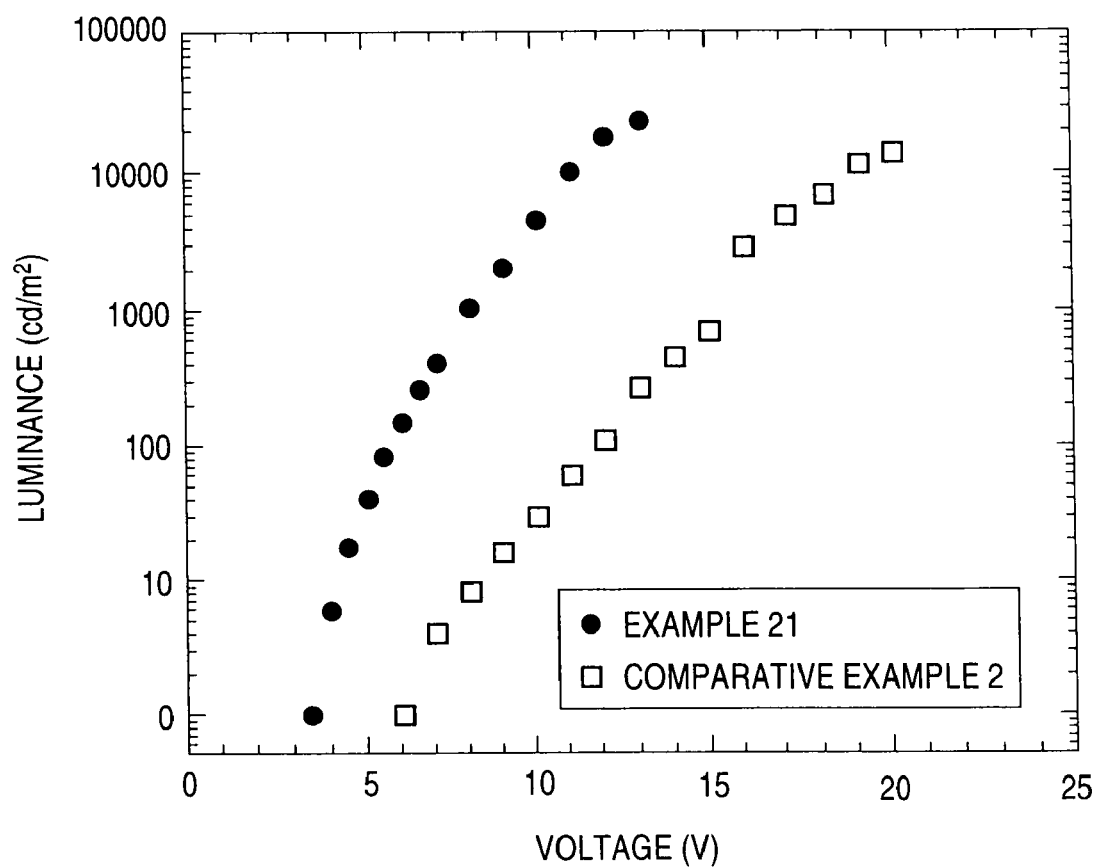
FIG. 10 is a graph comparing voltage/luminance characteristics between Example 21 and Comparative Example 2.
Figure 11:
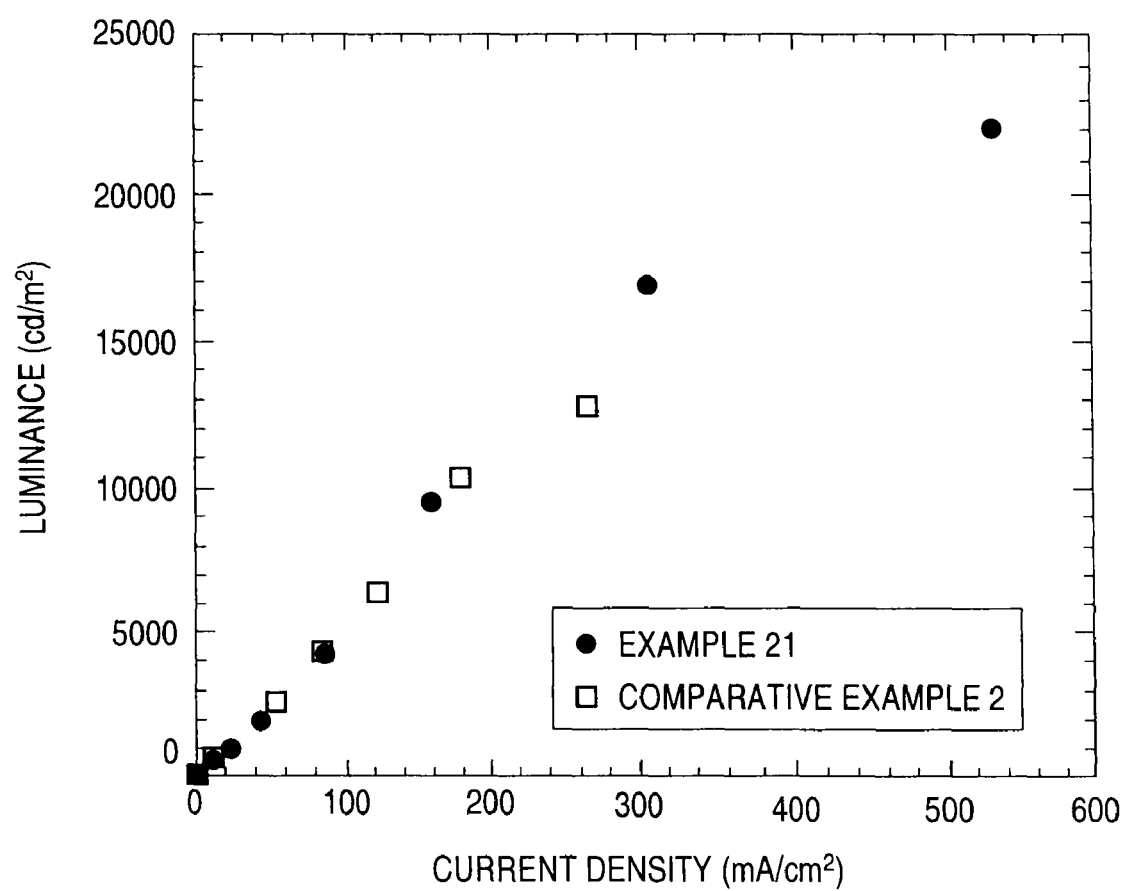
FIG. 11 is a graph comparing current density/luminance characteristics between Example 21 and Comparative Example 2.
Figure 12:
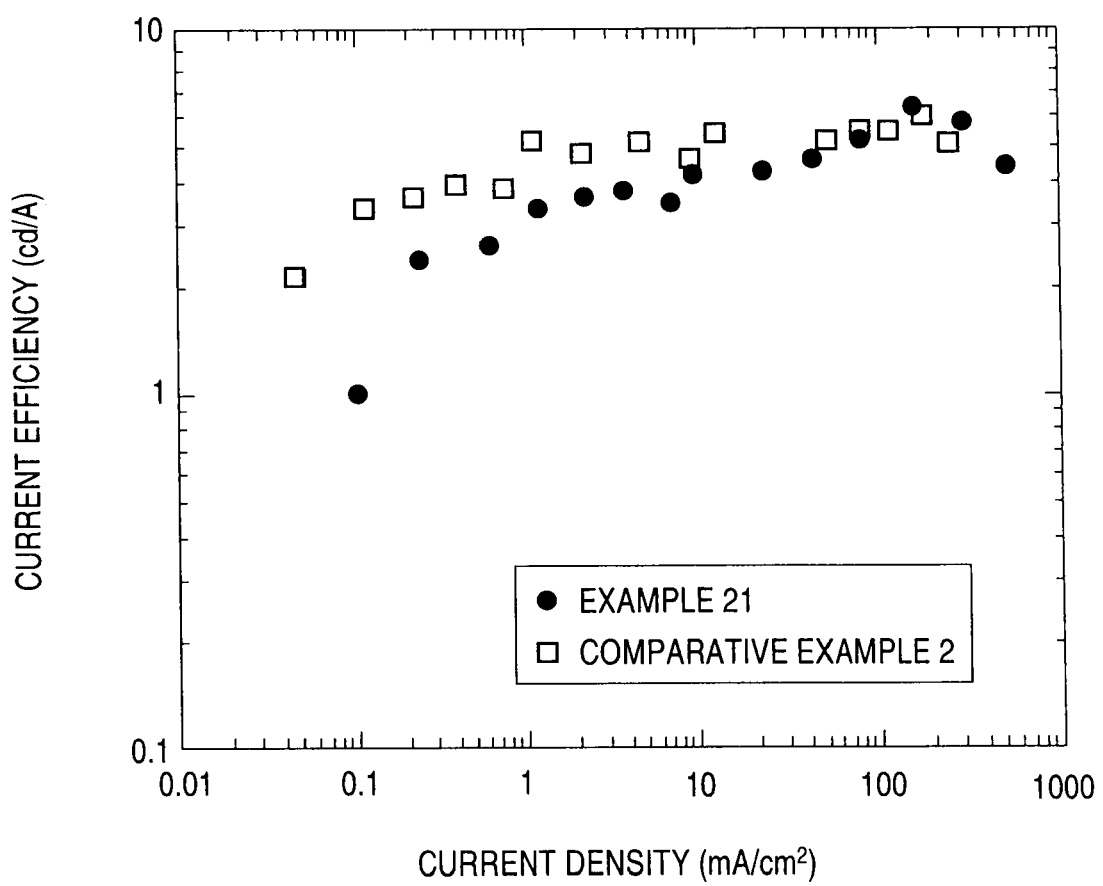
FIG. 12 is a graph comparing current density/current efficiency characteristics between Example 21 and Comparative Example 2.

An organic EL device as shown in FIG. 4 was prepared by depositing a hole transporting layer 4, an emission layer 5, an electron transporting layer 7, an electron injecting layer 8, and a cathode (aluminum electrode) 9 successively on an ITO electrode as a transparent anode 2 previously formed on a glass substrate 1. The glass substrate 1 having formed thereon ITO having a film thickness of 150 nm was washed with an organic solvent, and the surface thereof was washed with oxygen plasma treatment. This was fitted in a vacuum deposition machine, and pressure was reduced to 0.001 Pa or lower.

Subsequently, as the hole transporting layer 4, NPD was formed in about 50 nm at a deposition rate of 6 nm/min. Next, as the emission layer 5, Alq was formed in about 20 nm at a deposition rate of 6 nm/min. On this emission layer 5, as the electron transporting layer 7, CPBO (6) of the present invention was formed in about 30 nm at a deposition rate of 6 nm/min. Further, as the electron injecting layer 8, lithium fluoride was formed in about 0.5 nm at a deposition rate of 0.6 nm/min. The above depositions each were continuously conducted without breaking vacuum. Finally, a mask for cathode deposition was inserted, and aluminum was deposited in about 200 nm to form the cathode 9. The device prepared was stored in a vacuum desciccator, and characteristic measurement was conducted at ordinary temperature in atmosphere.

As a result of applying a direct current voltage to the organic EL device of the present invention thus prepared, emission of 100 cd/m² was observed from 3.5 V, and at 6.5 V, stable green emission of 10,000 cd/m² was obtained.

Example 24

An organic EL device was prepared under the same conditions as in Example 23, except that in the device of FIG. 4, the material of the electron transporting layer 7 was changed to PhpyOXDm (11) of the present invention, and the characteristics were examined.

Emission of 100 cd/m² was observed from 3.4 V. At 6.3 V, a stable green emission of 10,000 cd/m² was obtained.

Example 25

An organic EL device was prepared under the same conditions as in Example 23, except that in the device of FIG. 4, the material of the electron transporting layer 7 was changed to FPhpyOXDm (16) of the present invention, and the characteristics were examined.

Emission of 100 cd/m² was observed from 3.3 V. At 6.5 V, a stable green emission of 10,000 cd/m² was obtained.

Comparative Example 4

For the sake of comparison, an organic EL device was prepared under the same conditions as in Example 23, except that the material of the electron transporting layer 7 was changed to Alq, and the characteristics were examined. That is, as a layer serving as both emission layer 5 and electron transporting layer 7, Alq3 was formed in about 50 nm at a deposition rate of 6 nm/min. Emission of 100 cd/m² was observed at 3.9 V and emission of 10,000 cd/m² was obtained at 7.8 V.

Even in the comparative test in the case of using the electron injecting material, reduction in driving voltage is recognized. From this fact, it is predicted that electron mobility of the compound of the present invention is far higher than Alq which is the conventional electron transporting material.

Although the present invention has been described in detail and by reference to the specific embodiments, it is apparent to one skilled in the art that various modifications or changes can be made without departing the spirit and scope of the present invention.

This application is based on Japanese Patent Application No. 2004-088909 filed Mar. 25, 2004 and Japanese Patent Application No. 2004-089277 filed Mar. 25, 2004, the disclosures of which are incorporated herein by reference in their entities.

INDUSTRIAL APPLICABILITY

The compound having an oxadiazole ring structure having a substituted pyridyl group connected thereto, of the present invention is good in injection of electrons, high in electron mobility, and stable in a thin film state, and is therefore excellent as a compound for an organic EL device. By preparing an organic EL device using the compound, driving voltage can remarkably be reduced, and durability can be improved. For example, it becomes possible to spread the application to home appliances or illumination.

The invention claimed is:

1. An organic electroluminescence device comprising a pair of electrodes, and at least one organic layer interposed therebetween, wherein a compound having an oxadiazole ring structure having a substituted pyridyl group connected thereto, represented by the following general formula (1) is contained as a structural material of the at least one organic layer:

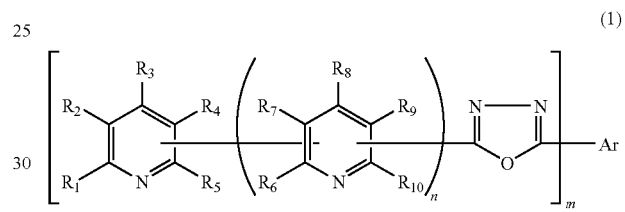

wherein Ar represents a substituted or unsubstituted aromatic hydrocarbon group, a substituted or unsubstituted aromatic heterocyclic group or a substituted or unsubstituted condensation polycyclic aromatic group; one of $R_1$, $R_2$, $R_3$, $R_4$ and $R_5$ is a linking group, and the others may be the same or different and represent a hydrogen atom, a fluorine atom, a cyano group, an alkyl group, a substituted or unsubstituted phenyl group or a substituted or unsubstituted naphthyl group; two of $R_6$, $R_7$, $R_8$, $R_9$ and $R_{10}$ are linking groups, and the others may be the same or different and represent a hydrogen atom, a fluorine atom, a cyano group, an alkyl group, a substituted or unsubstituted phenyl group or a substituted or unsubstituted naphthyl group; m is an integer of from 1 to 3; and n is an integer of from 2 to 4.

2. The organic electroluminescence device as claimed in claim 1, wherein n in the general formula (1) is 2.

3. The organic electroluminescence device as claimed in claim 1, wherein the compound represented by the general formula (1) is contained in an electron transporting layer.

4. The organic electroluminescence device as claimed in claim 1, wherein the compound represented by the general formula (1) is contained in a hole blocking layer.

5. The organic electroluminescence device as claimed in claim 1, wherein the compound represented by the general formula (1) is contained in an emission layer.

6. An organic electroluminescence device comprising a pair of electrodes, and at least one organic layer interposed therebetween, wherein a compound having an oxadiazole ring structure having a substituted pyridyl group connected thereto, represented by the following general formula (1) is contained as a structural material of the at least one organic layer:

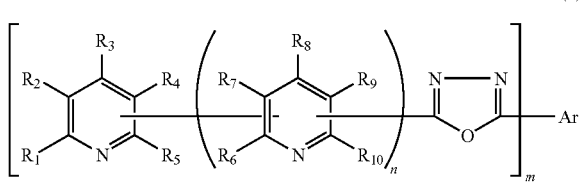

wherein Ar represents a substituted or unsubstituted aromatic hydrocarbon group, a substituted or unsubstituted aromatic heterocyclic group or a substituted or unsubstituted condensation polycyclic aromatic group; one of $R_1$, $R_2$, $R_3$, $R_4$ and $R_5$ is a linking group, and the others may be the same or different and represent a hydrogen atom, a fluorine atom, a cyano group, an alkyl group, a substituted or unsubstituted phenyl group or a substituted or unsubstituted naphthyl group; two of $R_6$, $R_7$, $R_8$, $R_9$ and $R_{10}$ are linking groups, and the others may be the same or different and represent a hydrogen atom, a fluorine atom, a cyano group, an alkyl group, a substituted or unsubstituted phenyl group or a substituted or unsubstituted naphthyl group; m is an integer of from 2 to 3; and n is an integer of from 0 to 4, provided that when n=0, four groups of $R_1$, $R_2$, $R_3$, $R_4$ and $R_5$ excluding the linking group are not simultaneously a hydrogen atom.

7. The organic electroluminescence device as claimed in claim 6, wherein n in the general formula (1) is 1.

8. The organic electroluminescence device as claimed in claim 6, wherein n in the general formula (1) is 2.

9. The organic electroluminescence device as claimed in claim 6, wherein n in the general formula (1) is 0, and one of four groups of $R_1$, $R_2$, $R_3$, $R_4$ and $R_5$ excluding the linking group is a phenyl group.

10. The organic electroluminescence device as claimed in claim 6, wherein the compound represented by the general formula (1) is contained in an electron transporting layer.

11. The organic electroluminescence device as claimed in claim 6, wherein the compound represented by the general formula (1) is contained in a hole blocking layer.

12. The organic electroluminescence device as claimed in claim 6, wherein the compound represented by the general formula (1) is contained in an emission layer.

13. An organic electroluminescence device comprising a pair of electrodes, and at least one organic layer interposed therebetween, wherein a compound having an oxadiazole ring structure having a substituted pyridyl group connected thereto, represented by the following general formula (1) is contained as a structural material of the at least one organic layer:

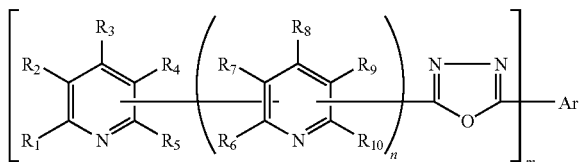

wherein Ar represents a substituted or unsubstituted aromatic hydrocarbon group, a substituted or unsubstituted aromatic heterocyclic group or a substituted or unsubstituted condensation polycyclic aromatic group; one of $R_1$, $R_2$, $R_3$, $R_4$ and $R_5$ is a linking group, and the others may be the same or different and represent a hydrogen atom, a fluorine atom, a cyano group, an alkyl group, a substituted or unsubstituted phenyl group or a substituted or unsubstituted naphthyl group; and at least one of $R_1$, $R_2$, $R_3$, $R_4$ and $R_5$ is an unsubstituted phenyl group; two of $R_6$, $R_7$, $R_8$, $R_9$ and $R_{10}$ are linking groups, and the others may be the same or different and represent a hydrogen atom, a fluorine atom, a cyano group, an alkyl group, a substituted or unsubstituted phenyl group or a substituted or unsubstituted naphthyl group; m is an integer of from 1 to 3; and n is an integer of from 0 to 4, provided that when n=0, four groups of $R_1$, $R_2$, $R_3$, $R_4$ and $R_5$ excluding the linking group are not simultaneously a hydrogen atom.

14. The organic electroluminescence device as claimed in claim 13, wherein n in the general formula (1) is 1.

15. The organic electroluminescence device as claimed in claim 13, wherein n in the general formula (1) is 2.

16. The organic electroluminescence device as claimed in claim 13, wherein the compound represented by the general formula (1) is contained in an electron transporting layer.

17. The organic electroluminescence device as claimed in claim 13, wherein the compound represented by the general formula (1) is contained in a hole blocking layer.

18. The organic electroluminescence device as claimed in claim 13, wherein the compound represented by the general formula (1) is contained in an emission layer.

19. An organic electroluminescence device comprising a pair of electrodes, and at least one organic layer interposed therebetween, wherein a compound having an oxadiazole ring structure having a substituted pyridyl group connected thereto, represented by the following general formula (1) is contained as a structural material of the at least one organic layer:

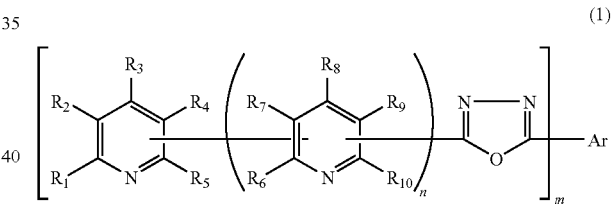

wherein Ar represents a substituted or unsubstituted aromatic hydrocarbon group, an unsubstituted aromatic heterocyclic group, or a substituted or unsubstituted condensation polycyclic aromatic group; one of $R_1$, $R_2$, $R_3$, $R_4$ and $R_5$ is a linking group, and the others may be the same or different and represent a hydrogen atom, a fluorine atom, a cyano group, an alkyl group, a substituted or unsubstituted phenyl group or a substituted or unsubstituted naphthyl group; two of $R_6$, $R_7$, $R_8$, $R_9$ and $R_{10}$ are linking groups, and the others may be the same or different and represent a hydrogen atom, a fluorine atom, a cyano group, an alkyl group, a substituted or unsubstituted phenyl group or a substituted or unsubstituted naphthyl group; m is an integer of from 1 to 3; and n is an integer of from 0 to 4, provided that when n=0, four groups of $R_1$, $R_2$, $R_3$, $R_4$ and $R_5$ excluding the linking group are not simultaneously a hydrogen atom.

20. The organic electroluminescence device as claimed in claim 19, wherein n in the general formula (1) is 1.

21. The organic electroluminescence device as claimed in claim 19, wherein n in the general formula (1) is 2.

22. The organic electroluminescence device as claimed in claim 19, wherein n in the general formula (1) is 0, and one of four groups of $R_1$, $R_2$, $R_3$, $R_4$ and $R_5$ excluding the linking group is a phenyl group.

23. The organic electroluminescence device as claimed in claim 19, wherein the compound represented by the general formula (1) is contained in an electron transporting layer.

24. The organic electroluminescence device as claimed in claim 19, wherein the compound represented by the general formula (1) is contained in a hole blocking layer.

25. The organic electroluminescence device as claimed in claim 19, wherein the compound represented by the general formula (1) is contained in an emission layer.

* * * * *